United States Patent
Nilson

[19]
[11] Patent Number: 6,009,868
[45] Date of Patent: *Jan. 4, 2000

[54] ARRANGEMENT IN A SPRAY TUBE MOUTHPIECE

[75] Inventor: Billy Nilson, Mjölby, Sweden

[73] Assignee: Astra AB, Sweden

[ * ] Notice: This patent issued on a continued prosecution application filed under 37 CFR 1.53(d), and is subject to the twenty year patent term provisions of 35 U.S.C. 154(a)(2).

[21] Appl. No.: 08/718,584

[22] PCT Filed: Jul. 4, 1996

[86] PCT No.: PCT/SE96/00910

§ 371 Date: Oct. 2, 1996

§ 102(e) Date: Oct. 2, 1996

[87] PCT Pub. No.: WO97/07897

PCT Pub. Date: Mar. 6, 1997

[30] Foreign Application Priority Data

Aug. 31, 1995 [SE] Sweden ................................. 9502999

[51] Int. Cl.[7] .................................................. A61M 11/00
[52] U.S. Cl. ................................ 128/200.18; 128/200.14; 128/203.12
[58] Field of Search .......................... 128/200.14, 200.15, 128/200.18, 203.12, 203.23, 203.24, 207.14; 239/461, 468–470, 490–492

[56] References Cited

U.S. PATENT DOCUMENTS

| | | | |
|---|---|---|---|
| 318,930 | 5/1885 | Sutton | 128/200.14 |
| 539,961 | 5/1895 | Russell | 128/200.14 |

(List continued on next page.)

FOREIGN PATENT DOCUMENTS

| | | |
|---|---|---|
| 348 638 | 1/1990 | European Pat. Off. . |
| 412 524 | 2/1991 | European Pat. Off. . |
| 439 109 | 7/1991 | European Pat. Off. . |
| 536 529 | 4/1993 | European Pat. Off. . |
| 2 522 537 | 9/1983 | France . |
| 16 25 235 | 3/1972 | Germany . |
| 34 43 640 | 6/1986 | Germany . |
| 13349 | 8/1912 | United Kingdom .................. 239/490 |

(List continued on next page.)

OTHER PUBLICATIONS

Dialog abstract of German counterpart of WO 89/05195 (listed above as document AL1), Derwent World Patents Index accession No. 89–192590/198926.

Dialog abstract of German counterpart of WO 94/27729 (listed above as document AN1), Derwent World Patents Index accession number 95–022530/199503.

Dialog abstract of French patent FR 2 522 537 (listed on p. 2 as document AP2), Derwent World Index accession No. 83–784779–198341.

(List continued on next page.)

*Primary Examiner*—Aaron J. Lewis
*Attorney, Agent, or Firm*—Michael A. Sanzo; Vinson & Elkins L.L.P.

[57] ABSTRACT

The present invention relates to a spray mouthpiece arranged on the outer free end of a spray tube. The mouthpiece is adapted by means of intersecting flow passages to atomize liquid which is fed to the spray tube under pressure. The arrangement according to the invention comprises an elongated sleeve which is adapted to be carefully placed on the free end of the spray tube. The sleeve is designed with an end face on which is a centrally located mouthpiece opening. In the sleeve is a cylindrical body connecting to the end face. The body has grooves with which the sleeve forms at least two ducts communicating with the tube. From the tube end, the ducts run approximately axially up to the end face. By means of the intersecting flow passages formed on the end face of the body, the ducts are connected to a chamber that connects to the mouthpiece opening.

5 Claims, 1 Drawing Sheet

6,009,868
Page 2

U.S. PATENT DOCUMENTS

| | | | |
|---|---|---|---|
| 932,718 | 8/1909 | Rachmann | 128/200.14 |
| 1,655,678 | 1/1928 | Dorment | 128/200.14 |
| 2,668,084 | 2/1954 | Saxton | 239/491 |
| 3,226,040 | 12/1965 | Briechle et al. | 239/492 |
| 3,406,911 | 10/1968 | Keeney | 239/490 |
| 3,595,479 | 7/1971 | Freeman | 239/468 |
| 3,724,763 | 4/1973 | Braun | 239/490 |
| 3,771,728 | 11/1973 | Polnauer . | |
| 4,678,123 | 7/1987 | Klaeger . | |
| 4,767,416 | 8/1988 | Wolf et al. | 128/200.14 |
| 4,923,448 | 5/1990 | Ennis, III | 128/200.14 |
| 5,067,655 | 11/1991 | Farago et al. . | |
| 5,224,471 | 7/1993 | Marelli et al. . | |
| 5,533,501 | 7/1996 | Denyer | 128/200.14 |
| 5,553,501 | 7/1996 | Denyer . | |

FOREIGN PATENT DOCUMENTS

| | | | |
|---|---|---|---|
| 244460 | 6/1926 | United Kingdom | 239/490 |
| 2 076 696 | 12/1981 | United Kingdom . | |
| WO 89/05195 | 6/1989 | WIPO . | |
| WO 89/06164 | 7/1989 | WIPO . | |
| WO 94/27729 | 12/1994 | WIPO . | |
| 9500195 | 1/1995 | WIPO | 128/200.14 |
| WO 95/00195 | 1/1995 | WIPO . | |

OTHER PUBLICATIONS

Dialog abstract of German patent DE 34 43 640 (listed on p. 3 as document AL3), Derwent World Patents Index accession No. 86–145384–198623.

Dialog abstract of German patent DE 16 25 235 (listed on p. 3 as document AM3), Derwent World Patents Index accession No. 77–C9573Y/197715.

English abstract of Soviet Union patent 1380–786, Derwent World Patents Index accession No. 88–276752/39.

English abstract of Soviet Union patent SU 887–006.

English abstract of Soviet Union patent SU 889–118.

International Search Report for Swedish appl. 9502999–7 (priority appl. of PCT/SE96/00910).

ARRANGEMENT IN A SPRAY TUBE MOUTHPIECE

FIELD OF THE INVENTION

The present invention relates to an arrangement in a spray tube mouthpiece arranged on the outer free end of a spray tube, which mouthpiece is adapted by means of intersecting flow passages to atomize liquid which is fed to the spray tube under pressure.

BACKGROUND OF THE INVENTION

In order to obtain sufficiently good atomization for certain applications, for example for the atomization of a liquid anesthetic in the nose or throat, a mouthpiece designed according to this principle is often given an outside diameter which is so much greater than the outer diameter of the tube that treatment as described above may be perceived as disagreeable.

Solutions are known in which a mouthpiece for the atomization of a liquid is integrated with the tube, so that the latter has the same diameter along its entire length. Since this means that the mouthpiece does not differ visually from the tube, the mouthpiece may, by mistake, be cut off when seeking to adapt the length of the tube to special requirements.

The use of intersecting flow passages in order to obtain an increased atomization effect in a liquid in a spray mouthpiece is already known from DE-A-1 625 235. In this the helical groove of the arrangement has the outer circumferential surface on a cylindrical part centrally located in a body supporting the mouthpiece nozzle. Owing to the fact that grooves are arranged in both directions and with equal pitch, these intersect at a number of points. This leads to the flows in the ducts, which are formed by the passage and the body supporting the mouthpiece nozzle, being atomized at the said points of intersection.

SUMMARY OF THE INVENTION

The object of the present invention is to provide, at low cost, an arrangement in a spray tube mouthpiece arranged on the outer free end of a spray tube, which arrangement produces atomization of the liquid so that a mist jet with circular spray pattern can issue from the spray mouthpiece. By means of the said arrangement, a mouthpiece is produced which only has a marginally larger outside diameter than that of the tube and which can be used in such applications as, for example, the atomization of liquid anesthetic for intermittent spraying of nose or throat. In addition the arrangement is intended to give a mouthpiece which differs visually from the rest of the tube so that the mouthpiece is not cut off by mistake.

According to the invention this object is achieved in that the arrangement comprises an elongated sleeve adapted to be carefully placed on the said free end of the spray tube and designed with an end face which has a centrally located mouthpiece opening and a cylindrical body, located in the sleeve and essentially connecting with the end face, the body having recesses which with the sleeve form at least two ducts communicating with the tube, which from the tube end run approximately axially up to the end face, in which each duct is connected by the said intersecting flow passages, formed on the end face of the body, to a chamber connecting preferably coaxially with the mouthpiece opening.

According to a special characteristic of the invention, the mouthpiece opening narrows conically in the direction away from the said chamber.

So that the tube has a correct insertion depth in the sleeve, the body, according to another special characteristic of the invention, has on its side remote from the end face at least one contact surface for the spray tube end, determining the insertion depth of the spray tube in the sleeve.

In order to facilitate assembly and flow from the tube end into the ducts, the body located in the sleeve, according to another special characteristic of the invention, has symmetrically formed end surfaces with flow passages and chambers respectively.

A further special characteristic of the invention resides in the fact that the ducts at the end face are each divided into two flow passages, which each describe a part of an arc in opposing directions to one another along the circumference and finally connect to the chamber, crossing a corresponding flow passage, which connects from the opposite direction, between the said chamber and the periphery.

BRIEF DESCRIPTION OF THE DRAWINGS

A preferred embodiment of the invention will be further explained below with reference to the attached drawing in which.

DETAILED DESCRIPTION OF THE INVENTION

Figure 1:
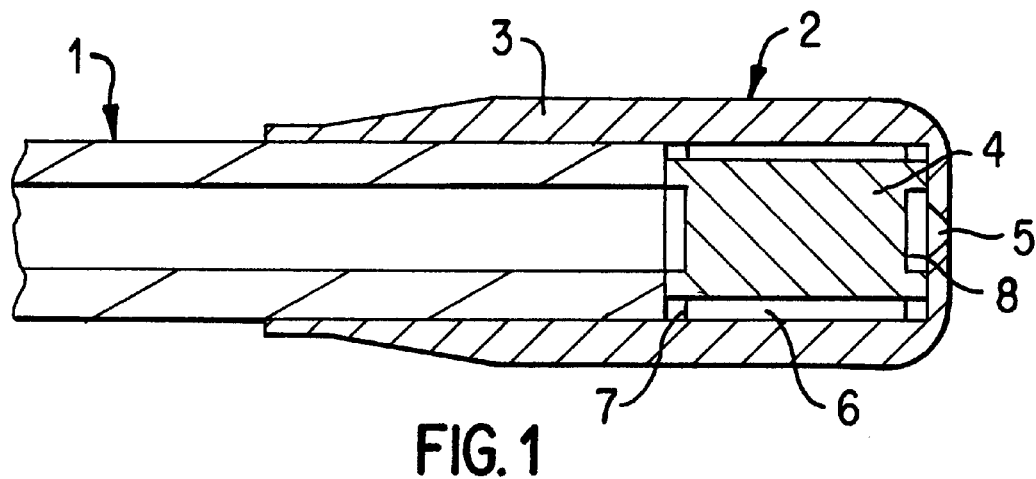
FIG. 1 is a longitudinal section showing the outer end of a tube provided with the arrangement according to the invention.

In FIG. 1, 1 generally denotes a tube which at its outer free end has a mouthpiece, generally denoted in the drawing by 2. The purpose of the mouthpiece 2 is to atomize a pressurized liquid in a reservoir, not shown in the drawing, to which the tube is connected.

According to the invention the spray tube mouthpiece 2 comprises two parts, an outer part 3 on the one hand and an inner part 4 on the other. The outer part 3 has the form of a cylindrical cup, which has an opening 5 in its base. The opening 5 serves as mouthpiece opening and narrows conically in the direction away from the said cup. The diameter of the spray pattern may be adjusted as a function of the opening angle of the opening 5.

The inner part 4 comprises a body, which is generally a cylinder, the outside diameter of which is chosen so that it fits into the outer part 3. It preferably has two axial grooves constituting ducts along the circumferential surface, which with the outer part 3 form ducts for the liquid which is to be atomized.

The outer part 3 is adapted to be carefully placed on the free end of the spray tube after first inserting the inner part 4 right into the outer part 3 and fitting against its base. The inner part 4 determines the insertion depth of the spray tube 1 in the outer part 3 by means of the contact surface, which is constituted by the end surface of the inner part 4 fitting against the tube 1. At its end surrounding the tube 1, the outer part 3 is connected to the tube 1, for example by ultrasonic welding or an equivalent method. The said connection is executed in such a way that there is no risk of the mouthpiece 2 according to the invention, which is placed on the tube end, becoming detached in use. The connection is tight so that liquid cannot flow back and out between the circumferential surface of the tube 1 and the outer part 3.

In order to facilitate assembly, the end surfaces of the inner part 4 are identically designed and formed with grooves 7 and chambers 8. The said grooves 7 together with base of the outer part 3 and the end of the tube respectively form flow passages 7 for the liquid. The flow passages 7 open into chambers 8, one of which communicates with the opening 5 in the base of the outer part 3 and the other of which communicates with the opening at the free end of the spray tube 1.

Figure 2:
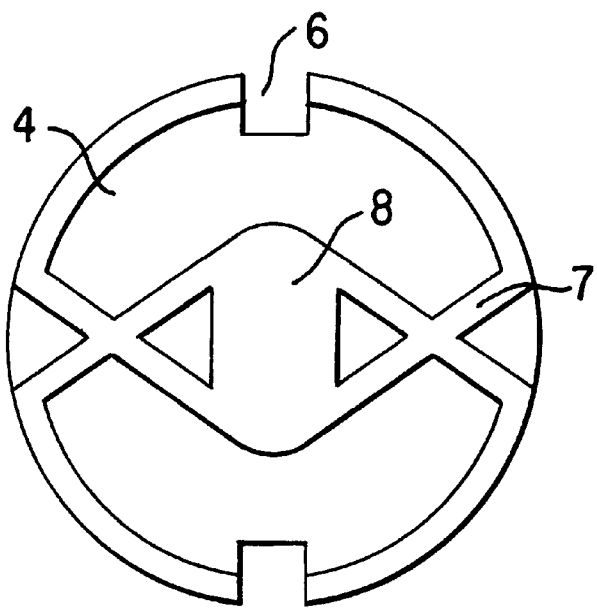
FIG. 2 is an end view of an inner part, the end surfaces of which are provided with intersecting flow passages.

As will be seen from FIG. 2, the flow passages 7 on the end surfaces of the inner part are arranged so that the ducts 6 at the end face are each divided into two flow passages 7. The said passages each describe a part of an arc in opposing directions to one another along the circumference. The flow passages 7 finally connect to the chamber 8, crossing a corresponding flow passage 7, which connects from the opposite direction, between the said chamber and the periphery. The flow passages 7 are also arranged so that the liquid flows meet one another in the chamber 8. This arrangement of the flow passages 7 results in a very good atomization of the liquid.

When the liquid is pumped out through the spray tube 1 and reaches the inner part 4, the liquid is forced into the chamber 8 and to the side through the flow passages 7 and into the ducts 6 on the side of the inner part 4. This is facilitated by the fact that both end surfaces of the inner part 4 are provided with grooves 7 and chambers 8.

The liquid is then forced through the ducts 6 to the front side of the inner part 4, where it continues through the flow passages 7 and is atomized by virtue of the fact that the latter are designed intersecting one another. The atomized liquid then continues to the chamber 8 where the flows are combined.

Thereafter the liquid is forced out through hole 5 in the base of the outer part 3, where it is further atomized and produces a circular spray pattern.

The fact that the outer part 3 has a somewhat larger diameter than the tube 1 means that the spray mouthpiece 2 differs visually from the rest of the spray tube 1, so that it is not cut off by mistake before use.

The invention is naturally not limited to the embodiment given above by way of an example, but lends itself to modifications within the idea of the invention described in the patent claims below.

I claim:

1. A combination comprising a spray tube (1) with a free end and a circumferential surface, and a spray mouthpiece attached to the free end of said spray tube and adapted by means of intersecting flow passages to atomize a liquid fed to the spray tube under pressure, said spray mouthpiece comprising:
    (a) an outer part (3) connected to the spray tube (1) in such a manner that fluid cannot flow out between the circumferential surface of the spray tube (1) and said outer part (3), wherein said outer part (3) has a centrally located mouthpiece opening (5); and
    (b) a cylindrical body (4) located in the outer part (3) and connected to said outer part (3), wherein the cylindrical body (4) has grooves which, with the outer part (3), form at least two ducts (6), wherein said ducts connect to intersecting flow passages (7), said flow passages (7) being also connected to a chamber (8), wherein said chamber is connected to said mouthpiece opening (5).

2. The combination of claim 1, wherein said mouthpiece opening is conically narrowed in the direction away from said chamber.

3. The combination of claim 1, wherein said cylindrical body has at least one contact surface for said spray tube and wherein said cylindrical body determines the insertion depth of said spray tube in said outer part.

4. The combination of claim 1, wherein said cylindrical body has symmetrically designed end surfaces with flow passages and chambers.

5. The combination of claim 1, wherein said ducts are divided into two flow passages, with each describing part of an arc in an opposing direction to the other and connecting to said chamber, crossing a corresponding flow passage which connects to said chamber from the opposite direction.

* * * * *